(12) United States Patent
Kramer

(10) Patent No.: US 11,398,308 B2
(45) Date of Patent: Jul. 26, 2022

(54) PHYSIOLOGIC SEVERITY OF ILLNESS SCORE FOR ACUTE CARE PATIENTS

(71) Applicant: CERNER INNOVATION, INC., Kansas City, KS (US)

(72) Inventor: Andrew A. Kramer, Leesburg, VA (US)

(73) Assignee: CERNER INNOVATION, INC., North Kansas City, MO (US)

( * ) Notice: Subject to any disclaimer, the term of this patent is extended or adjusted under 35 U.S.C. 154(b) by 989 days.

(21) Appl. No.: 14/585,845

(22) Filed: Dec. 30, 2014

(65) Prior Publication Data

US 2016/0188832 A1 Jun. 30, 2016

(51) Int. Cl.
*G16H 50/30* (2018.01)
*G16H 10/60* (2018.01)

(52) U.S. Cl.
CPC ............. *G16H 50/30* (2018.01); *G16H 10/60* (2018.01)

(58) Field of Classification Search
CPC ...... G06F 19/00; G06Q 10/087; G06Q 50/22; G16H 40/20
See application file for complete search history.

(56) References Cited

U.S. PATENT DOCUMENTS

| 2005/0086076 | A1 | 4/2005 | Dunn et al. |
| 2005/0197865 | A1 | 9/2005 | Jordan |
| 2007/0143142 | A1 | 6/2007 | Villasenor et al. |
| 2009/0005650 | A1 | 1/2009 | Angell et al. |
| 2009/0216556 | A1* | 8/2009 | Martin ................... G16H 40/63 705/3 |
| 2010/0057490 | A1 | 3/2010 | Kocis et al. |
| 2010/0076321 | A1* | 3/2010 | Zhang .................. A61B 5/4878 600/483 |

(Continued)

OTHER PUBLICATIONS

Wagner et. al ; "Acute physiology and chronic health evaluation (APACHE II) and Medicare reimbursement"; "Health Care Financing Review:Nov. 1984"; p. 91-105 https://www.cms.gov/Research-Statistics-Data-and-Systems/Research/HealthCareFinancingReview/Downloads/CMS1190362dl.pdf (Year: 1984).*

(Continued)

*Primary Examiner* — Reginald R Reyes
(74) *Attorney, Agent, or Firm* — Shook Hardy & Bacon LLP

(57) ABSTRACT

Systems, methods, and computer storage media are provided for determining a patient's severity of illness score (pSIS) for a patient admitted to an acute care facility. Data corresponding to physiologic components is received from an electronic medical record associated with a patient admitted to an acute care healthcare facility. The physiologic components include vital sign measurements and laboratory tests. Weights are assigned to a minimum, median, and maximum measured values for each vital sign. Weights are assigned to minimum and maximum values for each laboratory test. The weights are derived based on a deviation from normal within a time period. A pSIS is determined by summing the weights. Additional data corresponding to physiologic components may be received from the electronic medical record. The additional data may be utilized to update the weights and determine a patient's updated pSIS that may be utilized to track a progress of the patient.

16 Claims, 5 Drawing Sheets

(56) References Cited

U.S. PATENT DOCUMENTS

2012/0290319 A1 11/2012 Saria et al.
2013/0080373 A1* 3/2013 Yeck ..................... G16B 45/00
  706/50
2016/0188833 A1 6/2016 Kramer

OTHER PUBLICATIONS

Final Office Action received for U.S. Appl. No. 14/585,951, dated Nov. 16, 2017, 24 pages.
Non-Final Office Action received for U.S. Appl. No. 14/585,951, dated May 31, 2018, 28 pages.
Preinterview First Office Action received for U.S. Appl. No. 14/585,951, dated Jun. 5, 2017, 5 pages.

* cited by examiner

PHYSIOLOGIC SEVERITY OF ILLNESS SCORE FOR ACUTE CARE PATIENTS

CROSS-REFERENCE TO RELATED APPLICATION

This application is related by subject matter to U.S. patent application Ser. No. 14/585,951, filed Dec. 30, 2014, entitled "SUPPORTIVE CARE SEVERITY OF ILLNESS SCORE COMPONENT FOR ACUTE CARE PATIENTS." The entirety of the aforementioned application is incorporated by reference herein.

BACKGROUND

Upon admission to an acute care facility, such as an Intensive Care Unit (ICU), Step-Down Unit (SDU), or general medical-surgical floor, predictive methodologies are used to quantify a patient's severity of illness (pSIS) and to estimate their in-facility mortality risk. These predictive methodologies provide health care industry stakeholders with normalized metrics by comparing derived predictive score values with observed outcomes. For example, health care agencies and the general public may use predictive score data for inter-ICU performance comparisons while researchers may use predictive score data to evaluate experimental therapies.

One such predictive methodology is the Acute Physiology and Chronic Health Evaluation (APACHE®) that is based on the view that the core mission of intensive care is to treat disease and maintain physiological homeostasis. A central metric of the APACHE® predictive methodology is the APACHE® score measuring a patient's SOI during the initial twenty-four hour period following the patient's admission to the ICU. The APACHE® score is a composite of three components including the Acute Physiology Score (APS), co-morbid conditions, and the effects of age. The three components are each weighted according to their relative impact on the patient's SOI.

These three components of the APACHE® score are used in over seventy logistic and/or linear regression models that form the APACHE® predictive methodology. A result of one such model provides an estimation of a patient's mortality risk prior to being discharged from the acute care facility. This logistic regression model involves 143 physiological variables, including those in the APS component, age, seven concomitant chronic conditions, the period of time between hospital and ICU admissions, 116 diagnostic categories, the admission source, and five additional clinical variables.

A key component of the APACHE® score is the APS component that reflects the patient's response to treatment during the initial twenty-four hour period following their admission to the ICU. The worst recorded values for seventeen measured physiological variables within the initial twenty-four hour period following a patient's admission are used to determine weights. Each of these weights is assigned to the corresponding physiological variable, which are then summed to derive the APACHE®'s APS component. Consequently, an SOI score derived from the APS component can only worsen during that initial twenty-four hour period. A predictive methodology to derive predictive scores that tracks a patient's progress as the patient's condition improves or deteriorates over time is needed. Predictive scores from such predictive methodologies would be useful to gauge a patient's status throughout the day or may be used by health care providers as a signal in an early warning system.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In various embodiments, methods, systems, and computer storage media are performing a method in a clinical computing environment for determining a patient's severity of illness score (pSIS) for patients admitted to an acute care healthcare facility. Data corresponding to physiologic components is received from an electronic medical record associated with a patient admitted to an acute care healthcare facility. The data is not required to correspond to physiologic components collected in or associated with an intensive care unit. Weights are assigned to each physiologic component. The weights are derived based on a deviation from normal. A pSIS is for the patient is determined by summing the weights. Additional data corresponding to the physiologic components may be received from the electronic medical record. The additional data may be utilized to update the weights and determine an updated pSIS for the patient which may be utilized to track a progress of the patient.

BRIEF DESCRIPTION OF THE DRAWINGS

Embodiments are described in detail below with reference to the attached drawing figures, wherein.

DETAILED DESCRIPTION

Figure 1:
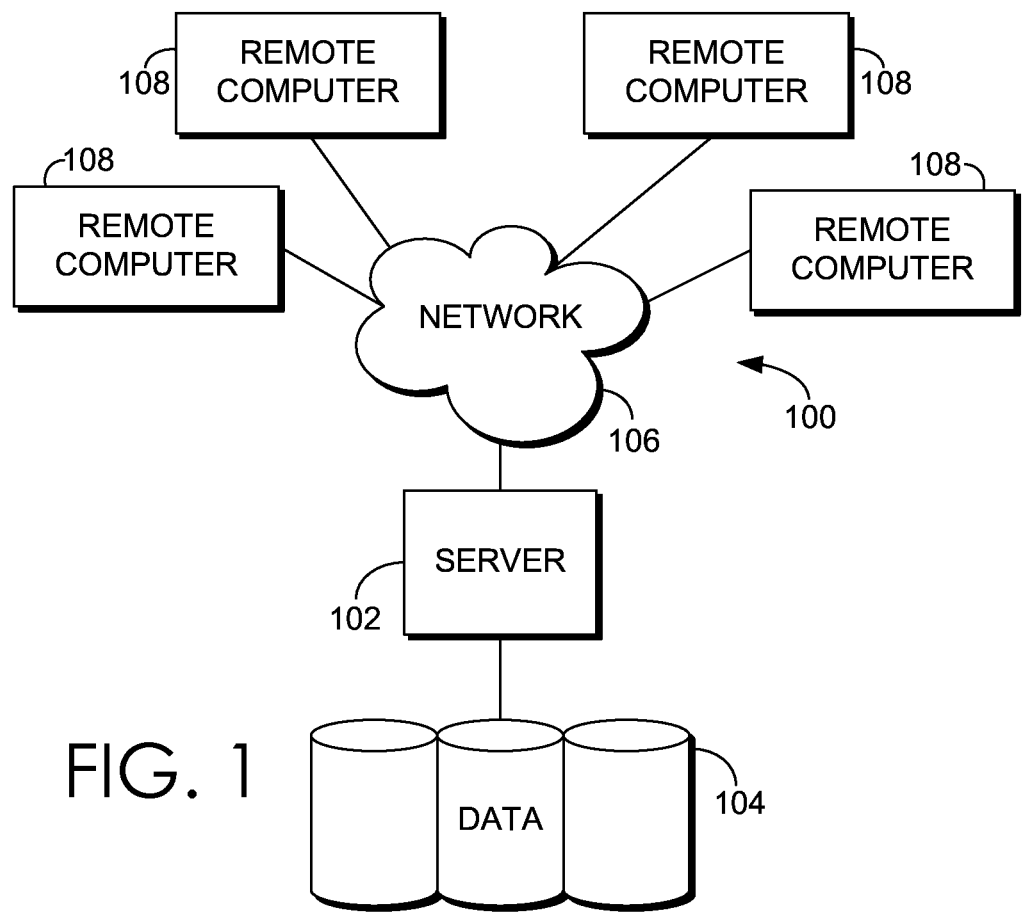
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Accordingly, various aspects of the technology described herein are generally directed to methods, systems, computer storage media useful for determining a pSIS for a patient admitted to an acute care healthcare facility. Various embodiments of the present invention are directed to determining a pSIS for a patient by summing weights assigned to physiologic components. In these embodiments, data associated with physiologic components are received from an electronic medical record associated with a patient. In some embodiments, an electronic medical record associated with a patient includes data from all admissions to an acute care facility. In these embodiments, the pSIS derived using such data could be used with a broader scope of patients admitted to the acute care facility, not just to an ICU.

In some embodiments, the received data includes data associated with a patient's vital sign measurements. In these embodiments, weights are assigned to a minimum, median, and maximum measured value for each of the vital sign measurements. In these embodiments, the weights associated vital sign measurements are derived based on a deviation from normal for minimum, median, and maximum measured values over a twenty-four hour time period following the patient's admission and subsequently updated as new values are recorded.

In some embodiments, the received data includes data associated with common laboratory tests on a blood sample taken from the patient. In these embodiments, weights are assigned to a minimum and a maximum measured value for each of the common laboratory tests. In these embodiments, the weights associated with common laboratory test measurements are derived based on a deviation from normal for minimum and maximum measured values over a twenty-four hour time period following the patient's admission and subsequently updated as new values are recorded.

Exemplary Computing Environment

Having briefly described an overview of embodiments of the invention, an exemplary computing environment suitable for use in implementing embodiments of the present invention is described below. Referring to the figures in general and initially to FIG. 1 in particular, an exemplary computing environment (e.g., medical-information computing-system environment) with which embodiments of the present invention may be implemented is depicted and designated generally as computing environment 100. Computing environment 100 is merely an example of one suitable computing environment and is not intended to suggest any limitation as to the scope of use or functionality of the invention. Neither should computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, computing environment 100 includes a computing device in the form of control server 102. Exemplary components of control server 102 comprise a processing unit, internal system memory, and a suitable system bus for coupling various system components, including data store 104, with control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media. Computer-readable media can be any available media that might be accessed by control server 102, and includes volatile and nonvolatile media, as well as, removable and non-removable media. By way of example, and not limitation, computer-readable media may comprise computer storage media and communication media. Computer storage media does not comprise, and in fact explicitly excludes, signals per se.

Computer storage media includes both volatile and non-volatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Control server 102 might operate in a computer network 106 using logical connections to one or more remote computers 108. Remote computers 108 might be located at a variety of locations in a medical or research environment or at healthcare facilities, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians or healthcare providers may comprise a treating physician or physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

Remote computers 108 may also be physically located in nontraditional medical care environments so that the entire healthcare community might be capable of integration on the network. Remote computers 108 may include personal computers, servers, routers, network PCs, peer devices, other common network nodes, or the like and might comprise some or all of the elements described above in relation to control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108.

For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization, a healthcare provider, and/or a user at a healthcare facility might enter commands and information into the control server 102 or convey the commands and information to control server 102 via one or more remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to control server 102. In addition to a monitor, control server 102 and/or remote computers 108 might comprise other peripheral output devices, such as speakers and a printer.

Although many other internal components of control server 102 and remote computers 108 are not shown, such components and their interconnection are well known. Accordingly, additional details concerning the internal construction of control server 102 and remote computers 108 are not further disclosed herein.

Figure 2:
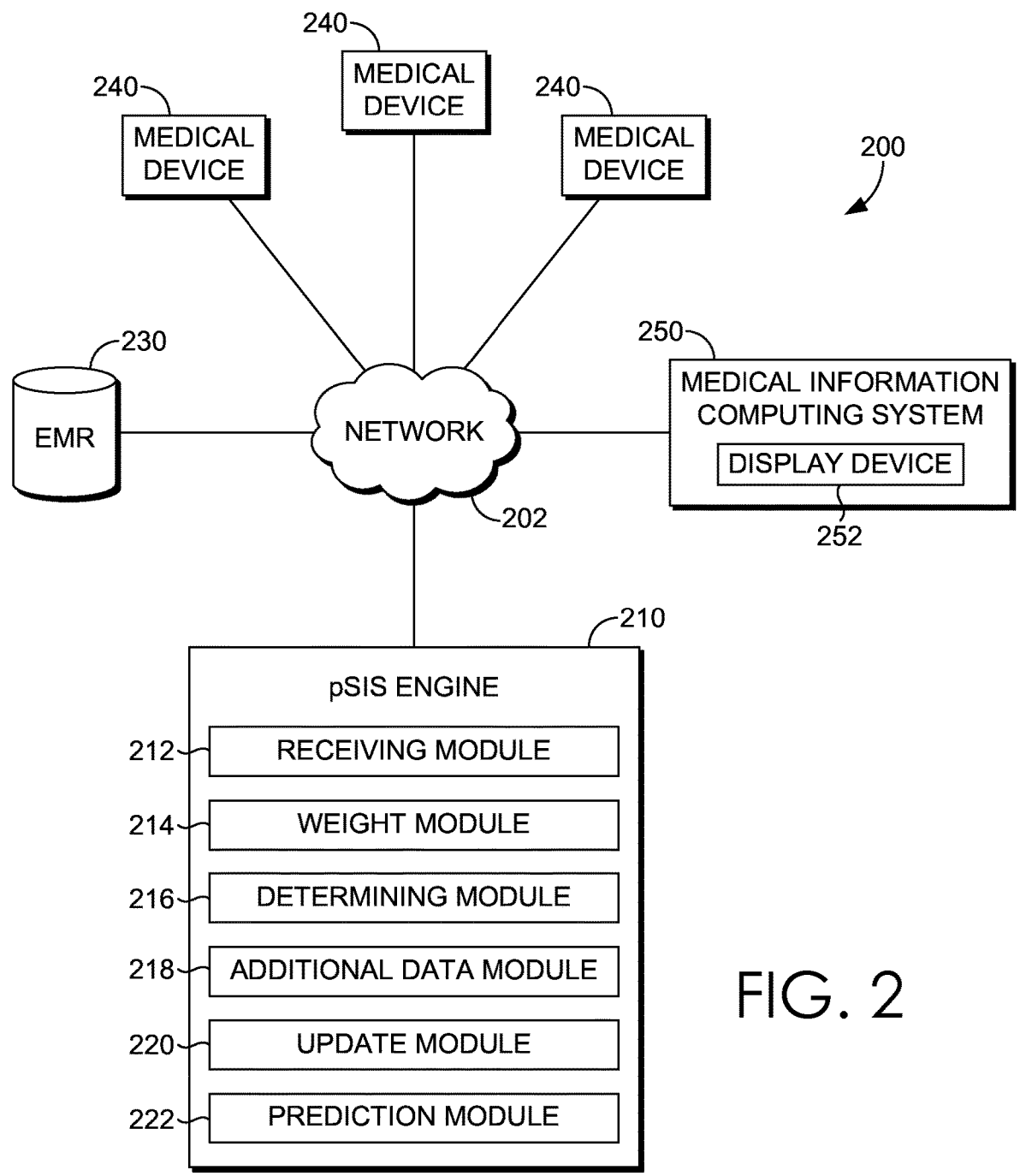
FIG. 2 is a block diagram of an exemplary clinical decision support rule generation and maintenance system, in accordance with embodiments of the present invention.

Referring now to FIG. 2, a block diagram is provided illustrating an exemplary system 200 in which a pSIS engine 210 is shown interfaced with medical information computing system 250 in accordance with an embodiment of the present invention. Medical information computing system 250 may be a comprehensive computing system within a clinical environment similar to the exemplary computing system 100 discussed above with reference to FIG. 1.

Medical information computing system 250 includes a clinical display device 252. In one embodiment, clinical display device 252 is configured to display a pSIS score as determined by pSIS engine 210. In another embodiment, clinical display device 252 is configured to receive input from the clinician, such as selection of a patient type, unit, facility information, or information associated with the patient, and the like. In another embodiment, medical information computing system 250 receives inputs, such as information associated with a patient, from one or more medical devices 240.

In general, pSIS engine 210 is configured to determine a pSIS for a patient admitted to an acute care facility. As shown in FIG. 2, pSIS engine 210 includes, in various embodiments, receiving module 212, weight module 214, determining module 216, additional data module 218, update module 220, and prediction module 222.

Receiving module 212 is configured to receive data corresponding to physiologic components from one or more electronic medical records associated with a patient admitted to an acute care facility. The data is associated with a patient's vital signs and common laboratory tests on a blood sample taken from the patient.

Weight module 214 is configured to assign weights to each physiologic component or measure of interest. The weights are derived based on a deviation from normal of a minimum, a median, and/or a maximum measured value. A genetic algorithm (GA) methodology is utilized, in one embodiment, to assign cut-points that define intervals of each physiologic measurement and weights that are assigned to each interval defined for the physiologic measures of interest. Genetic algorithms are adaptive machine learning models that mimic aspects of biological evolution like the principles of natural selection, inheritance, and variation to potentially optimize solutions to a problem.

Initially, the cut-point and weight for each component are assigned a random value. These randomly assigned values for each component's cut-point and weight represent an initial population of potential solutions to the problem. For example, the problem could be predicting a patient's mortality risk prior to being discharged from an acute care facility. The set of solutions from this initial population serve as inputs to the GA algorithm. Each component's cut-point and weight are evaluated based upon an objective standard known as a fitness function. In general, the fitness function is a metric specifically tailored for the problem. For example, the fitness function could be a metric of how accurate a particular set of solutions is at predicting a patient's mortality risk prior to being discharged from an acute care facility.

The evaluation process begins by assigning fitness values to each member (i.e. cut-point and/or weight) of the initial population, which may serve as a basis for a selection process. During the selection process members of the initial population with low fitness values may be eliminated. Members with high fitness values may be selected as "parents" that are used to produce a succeeding population of "children". Upon selection, GA operators like mutation operators and crossover operators are applied to those selected parents to produce the succeeding population. GA operators serve to probabilistically introduce random variations into the succeeding population to prevent such things as a particular set of solutions converging towards local optima.

This process cycle of evaluation, selection, and application of GA operators is repeated until some condition is satisfied. These conditions may include a particular population meets a threshold level of accuracy, a threshold number of cycle iterations have been performed, or any predetermined threshold established by a user. Once the condition is satisfied, this approach yields cut-points that define ranges for physiologic measurements of interest and weights that are assigned to each of those particular ranges. Therefore, when this cycle of evaluation, selection, and genetic operations is iterated for many several generations, the overall fitness of the population generally improves, on average. The resulting set of solutions in the final population represents improved "solutions" to the problem.

In one embodiment, seven physiologic measures of interest include four items related to vital sign information used by the APACHE® predictive methodology (Heart Rate (HR), Respiratory Rate (Resp), Temperature (Temp), and Mean Arterial Pressure (MAP)) as well as three items related to common laboratory tests on a blood sample from the patient (Platelet Count, Hematocrit, and Sodium). Similar to APACHE®'s APS component, a pSIS includes four vital sign physiologic measures of interest, including the minimum and maximum measured values over a twenty-four hour time period. Unlike the APACHE®'s APS component, the pSIS utilizes each vital sign's median measured value over a time period, which might improve during that time frame. In an embodiment, the time period may be twenty-four hours. Notably, the present invention utilizes a Platelet Count measurement that is not included by the APACHE® methodology. Platelet count imparts information on the body's ability to clot a wound. Too small a value implies inability to heal a wound, while too large a value indicates the possibility of a blood clot. Platelet count is considered an important laboratory test that should be included in a measure of physiologic derangement. The present invention excludes nine physiologic measures that were part of APACHE's APS, as these measures were found to be of little importance by the GA and/or infrequently measured.

In one embodiment, the four physiologic measures of interest available via vital sign measurements are utilized with the cut-points (in parenthesis) and weights (before parenthesis) as shown below in Table 1.

In one embodiment, the three physiologic measures of interest available via laboratory tests on a blood sample are utilized with the cut-points (in parenthesis) and weights (before parenthesis) as shown below in Table 2.

TABLE 2

| | | |
|---|---|---|
| 4 (<27.10%) | Highest Hematocrit 0 (27.10-41.39%) | 5 (>41.39%) |
| 6 (<25.50%) | Lowest Hematocrit 0 (25.50-40.89%) | 5 (>41.39%) |
| 6 (<125 × $10^9$/L) | Highest Platelet 0 (125-321 × $10^9$/L) | 4 (>321 × $10^9$/L) |
| 10 (<119 × $10^9$/L) | Lowest Platelet 0 (119-314 × $10^9$/L) | 2 (>314 × $10^9$/L) |
| 5 (<134 mEq/L) | Highest Sodium 0 (134-143 mEq/L) | 9 (>143 mEq/L) |
| 11 (<133 mEq/L) | Lowest Sodium 0 (133-142 mEq/L) | 6 (>142 mEq/L) |

Determining module 216 is configured to determine a pSIS for the patient by summing weights associated with each minimum and maximum value measured for each physiologic component or measure of interest (and also each median value measured for vital sign physiologic components) using data received by receiving module 212 during the preceding time period with weights assigned by weight module 214. In embodiments, the preceding time period is the preceding twenty-four hours.

In embodiments where the received data is associated with a patient's vital sign measurements, the pSIS is determining by summing weights assigned to a minimum, a median, and a maximum measured vital sign value. In these embodiments, weight module 214 assigns weights based on a deviation from normal for minimum, median, and maximum for each measured vital sign values over a time period following the patient's admission.

In embodiments where the received data is further associated with common laboratory tests on a blood sample taken from the patient, the pSIS is determining by summing weights assigned to a minimum and a maximum measured value for each of the common laboratory tests. In these embodiments, weight module 214 assigns weights based on minimum and maximum measured values for each of the common laboratory tests over the time period.

TABLE 1

| | | | | | | |
|---|---|---|---|---|---|---|
| | | 5 (<64 $min^{-1}$) | Highest HR 0 (64-94 $min^{-1}$) | 5 (95-102 $min^{-1}$) | 9 (103-138 $min^{-1}$) | 16 (>138 $min^{-1}$) |
| | | 9 (<48 $min^{-1}$) | Lowest HR 0 (48-76 $min^{-1}$) | 2 (77-100 $min^{-1}$) | 13 (>100 $min^{-1}$) | |
| | | 3 (<57 $min^{-1}$) | Median HR 0 (64-94 $min^{-1}$) | 3 (72-80 $min^{-1}$) | 5 (81-87 $min^{-1}$) | 8 (88-111 $min^{-1}$) | 11 (>111 $min^{-1}$) |
| | | 6 (<76.00 mmHg) | Highest MAP 0 (76.00-93.66 mmHg) | 1 (93.67-136.32 mmHg) | 9 (>136.32 mmHg) | |
| 18 (<53.00 mmHg) | 10 (53.00-70.32 mmHg) | 5 (70.33-82.66 mmHg) | Lowest MAP 0 (82.67-103.99 mmHg) | 5 (>103.99 mmHg) | | |
| | 13 (<68.00 mmHg) | 4 (68.00-81.66 mmHg) | Median MAP 0 (81.67-88.71 mmHg) | 10 (88.72-115.16 mmHg) | 7 (>115.16 mmHg) | |
| | 15 (<36.11° C.) | 2 (36.11-36.79° C.) | Highest Temp. 0 (36.80-37.06° C.) | 3 (37.07-38.44° C.) | 9 (>38.44° C.) | |
| | | 14 (<35.11° C.) | Lowest Temp. 0 (35.11-35.99° C.) | 2 (36.00-36.12° C.) | 4 (36.13-36.99° C.) | 5 (>36.99° C.) |
| | | 6 (<36.44° C.) | Median Temp. 0 (36.44-36.61° C.) | 2 (36.62-37.60° C.) | 7 (>37.60° C.) | |
| | | 12 (<16 $min^{-1}$) | Lowest Resp. 0 (16-19 $min^{-1}$) | 16 (>19 $min^{-1}$) | | |
| | | 13 (<17 $min^{-1}$) | Highest Resp. 0 (17-19 $min^{-1}$) | 1 (20-23 $min^{-1}$) | 18 (>23 $min^{-1}$) | |
| | 2 (<14 $min^{-1}$) | 1 (14-17 $min^{-1}$) | Median Resp. 0 (18-19 $min^{-1}$) | 3 (20-22 $min^{-1}$) | 14 >22 $min^{-1}$) | |

In embodiments where the received data is associated with both a patient's vital sign measurements and common laboratory tests, a combination of the above assigned weights may be used to determine a pSIS. That is, the pSIS may be determined by a summation of both weights assigned to a minimum, a median, and a maximum for each measured vital sign value as well as a summation of weights assigned to a minimum and a maximum measured value for each of the common laboratory tests. In an embodiment, a pSIS can be determined by determining module 216 for the general patient population within an acute care facility.

For example, during an initial twenty-four hour period following admission of a patient to a health care facility, the following physiologic component measurements are received for a patient. The vital sign measurements include: heart rate measured values (maximum=118 min$^{-1}$, minimum=45 min$^{-1}$, and median=95 min$^{-1}$); MAP measured values (maximum=110 mmHg, minimum=80 mmHg, and median=92 mmHg), body temperature measured values (maximum=40.0° C., minimum=35.8° C., and median=37.3° C.), and respiratory rate measured values (maximum=17 min$^{-1}$, minimum=12 min$^{-1}$, and median=13.7 min$^{-1}$. In this example, the common laboratory test measurements include: platelet count measured values (maximum=350*10$^9$/L and minimum=110*10$^9$/L), hematocrit measured values (maximum=43% and minimum=40%), and sodium level measured values maximum=144 mEq/L and minimum=133 mEq/L).

Using the weight values provided in the embodiment shown in Table 1, the patient's weights for the maximum, median, and minimum recorded values, respectively, for each vital sign are: heart rate (maximum=9, median=8, and minimum=9); MAP (maximum=1, median=10, and minimum=5); body temperature (maximum=9, median=2, and minimum=0); and respiratory rate (maximum=0, median=2, and minimum=12). Using the weight values provided in the embodiment shown in Table 2, the patient's weights for the maximum and minimum recorded values, respectively, for each common laboratory test are: platelet count (maximum=4 and minimum=10); hematocrit (maximum=5 and minimum=0); and sodium level (maximum=9 and minimum=0). Accordingly, a pSIS for this fictional patient, determined by a summation of the weights, would be 95 [heart rate (9+8+9)+MAP (1+10+5)+body temperature (9+2+0)+respiratory rate (0+2+12)+platelet count (4+10)+hematocrit (5+0)+sodium level (9+0)].

Additional data module 218 is configured to receive additional data corresponding to the physiologic components from the electronic medical record. The additional data may be based on changes associated with the patient that might affect the weight for a particular physiologic component and/or the pSIS. The additional data may be based on a clinician's desire to monitor a particular physiologic component or a follow-up measurement for that physiologic component. Similarly, the additional data may be based on a follow-up visit or later admission (i.e., after the initial admission) to the acute care facility.

Update module 220 is configured to update the weights and determine an updated pSIS for the patient. In one embodiment, update module 220 assigns updated weights to each physiologic component. In another embodiment, update module 220 may communicate the additional data corresponding to the physiologic components to weight module 214 so weight module 214 can assign updated weights to each physiologic component. In one embodiment, weight module 214 communicates the updated weights to determining module 216 to determine the updated pSIS. In another embodiment, update module 220 determines the updated pSIS.

In some embodiments, the pSIS can be utilized as a component of an overall severity of illness (SOI) score and/or a variable in predictive equations. In these embodiments, such predictive equations may comprise: demographics, other medical conditions diagnosed for a patient, comorbid conditions, additional procedures/medications performed on or in use by a patient, and the like. Accordingly, in one embodiment, prediction module 222 may utilize the pSIS in a predictive equation to predict a likelihood of hospital mortality for the patient. In another embodiment, prediction module 222 may utilize the pSIS in a predictive equation to predict a length of stay in the acute care facility for the patient. In other embodiments, prediction module 222 may utilize the pSIS in a predictive equation to predict any of a plurality of outcomes for the patient including: duration of mechanical ventilation, location of stay (e.g. level of care), readmission risk, discharge destination, and the like.

Figure 3:
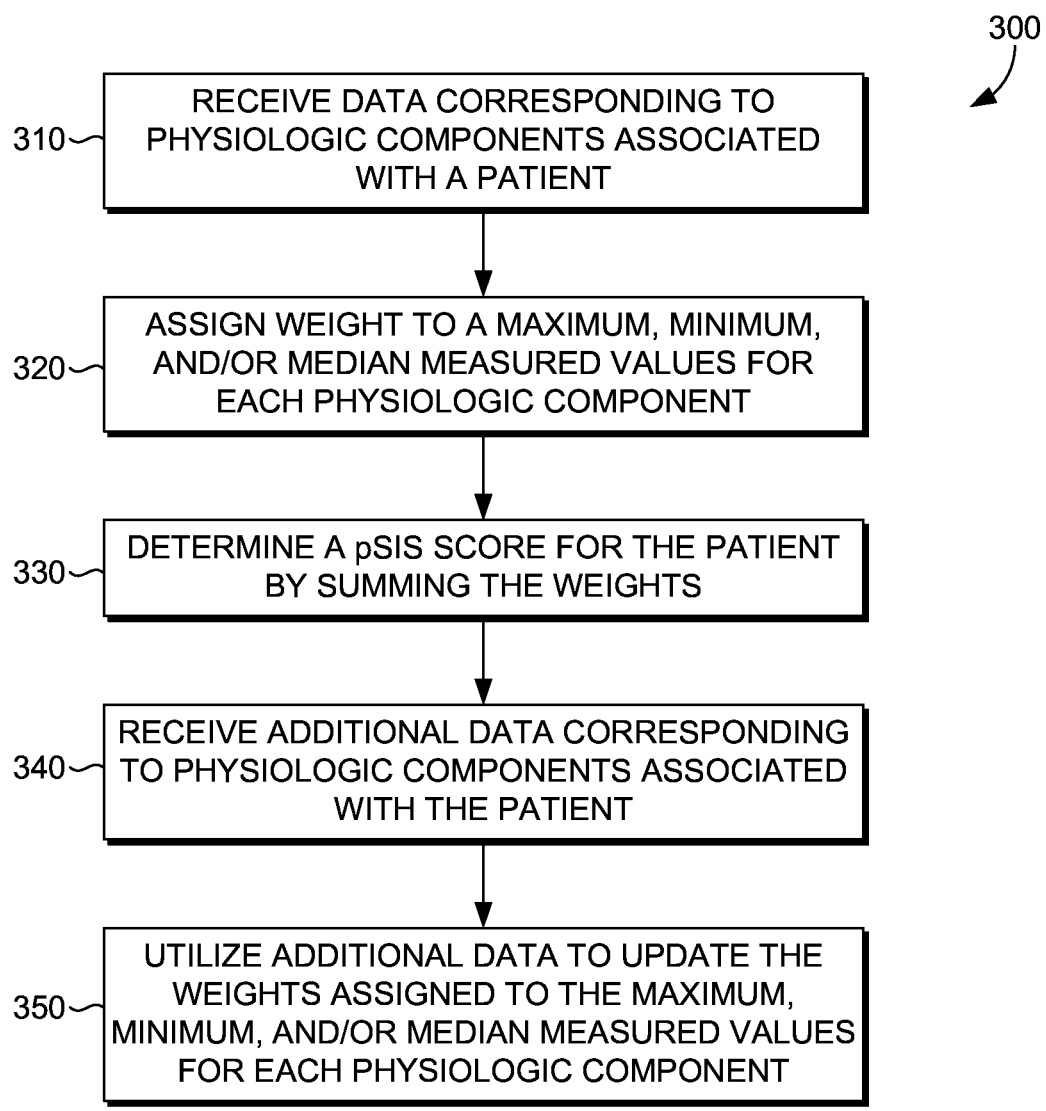
FIG. 3 is a flow diagram showing an exemplary method for determining a pSIS for a patient admitted to an acute care healthcare facility, in accordance with various embodiments of the present invention.

Turning now to FIG. 3, a flow diagram is provided illustrating a method 300 for determining a pSIS for a patient admitted to an acute care healthcare facility, in accordance with various embodiments of the present invention. Initially, in step 310 data corresponding to physiologic components is received from an electronic medical record associated with a patient admitted to an acute care healthcare facility.

In some embodiments, the data comprises information derived from the patient's vital sign measurements taken within an initial twenty-four period following admission. In these embodiments, the information derived from the patient's vital sign measurements includes a minimum, a median, a maximum, and/or a range of recorded measurement values. In other embodiments, the data comprises information derived from common laboratory tests performed on a blood sample taken from the patient. In these embodiments, the information derived from common laboratory tests performed on the blood sample includes a minimum, a maximum, and/or a range of recorded measurement values.

In step 320, weights are assigned to each physiologic component. The weights are derived based on a deviation from normal. A GA methodology may be utilized, as discussed above with respect to FIG. 2, to assign weights to each physiologic component. In embodiments where the data comprises vital sign measurement information, weights are assigned to a minimum, a median, and a maximum measured value for each vital sign physiologic component measured. In these embodiments, weights associated with each vital sign measurement are derived based on a deviation from normal for minimum, median, and maximum measured values over a time period following the patient's admission.

In embodiments where the data comprises common laboratory test information, weights are assigned to a minimum and a maximum measured value for each common laboratory test measurement. In these embodiments, weights associated with each common laboratory test derived based on a deviation from normal for minimum and maximum measured values over the time period following the patient's admission.

At step 330, a pSIS is determined for the patient by summing the derived weights. In some embodiments, the pSIS can be utilized as a component of an overall severity of illness (SOI) score and/or a variable in predictive equations. Additional data corresponding to the physiologic components is received, at step 340, from the electronic medical record. The additional data is utilized to update the weights and determine an updated pSIS for the patient at step 350.

In one embodiment, a progress of the patient is tracked based on the updated pSIS that is updated whenever a new measurement is recorded, and assessed over the preceding time period. For example, the preceding time period may be twenty-four hours. In another embodiment, by including weights assigned to median values for each vital sign measurement measured, a patient's pSIS score may improve or worsen (e.g. decrease or increase) over a period of time. For example, the period of time could be twenty-four hours. Accordingly, a clinician can compare the initial pSIS to subsequent updated pSIS's to determine whether a treatment is working or the patient is progressing appropriately. In some embodiments, updated pSIS's may be used to trigger alerts for clinicians associated with the patient's physiology. For example, updated pSIS's may be used to trigger emergency alerts/warnings about a patient's rapidly worsening physiology.

Figure 4:
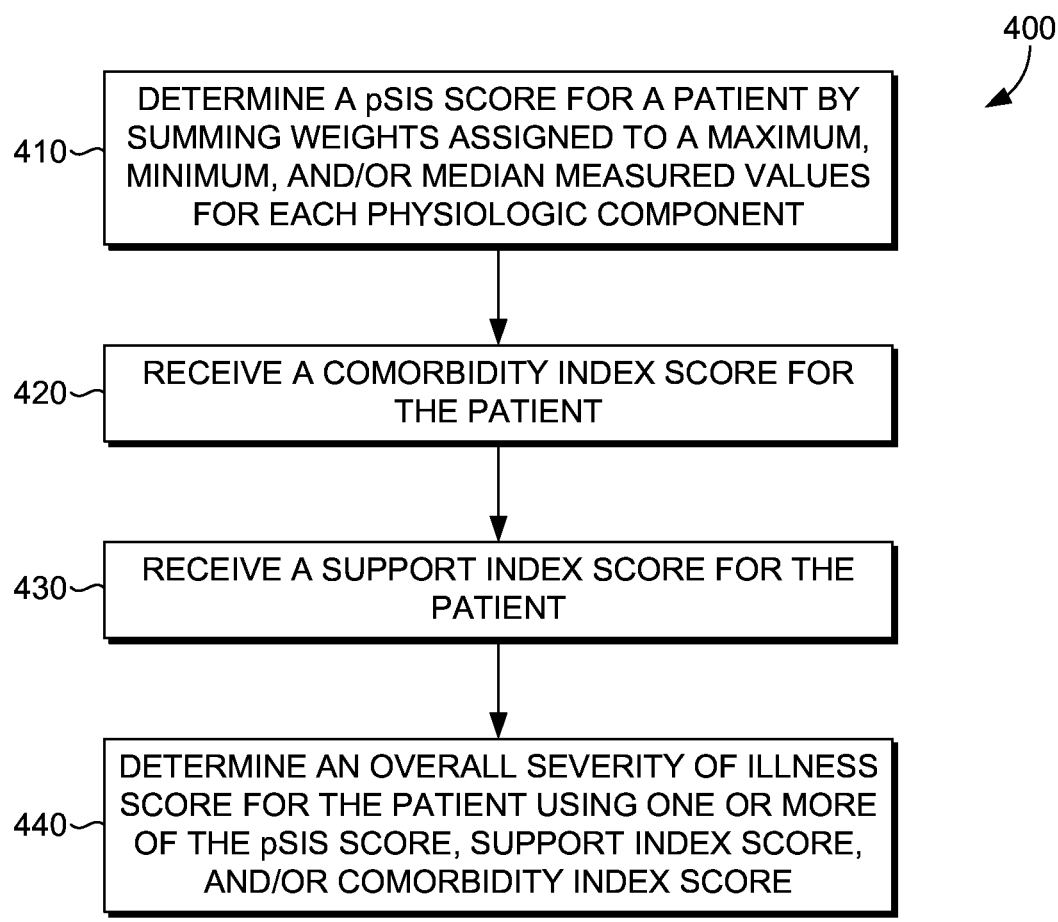
FIG. 4 is a flow diagram showing an exemplary method for determining an overall severity of illness score, using a pSIS as a component, in accordance with various embodiments of the present invention.

Turning now to FIG. 4, a flow diagram is provided illustrating a method 400 for determining an overall SOI score, using a pSIS as a component, for a patient admitted to an acute care healthcare facility, in accordance with various embodiments of the present invention. As discussed above, a pSIS, may be utilized as a component of an overall SOI score for the patient. Initially, in step 410, a pSIS and/or an updated pSIS is determined in accordance with method 300.

In an optional step 420, a comorbidity index (CI) score for the patient is received. When used with a pSIS as a component of an overall SOI score for a patient, the CI score accounts for effects that comorbidities have on a patient's physiology. In embodiments where a CI score is used, the CI score for a patient may be determined by summing weights assigned to one or more comorbidity variables identified in an electronic medical record associated with the patient. Also, in some embodiments, a multiplier may be applied to the summation of weights assigned to the one or more identified comorbidity variables (e.g. summation of weights*8).

In an embodiment, the one or more comorbidity variables and associated weights for each that are used to determine the CI score are shown in Table 3 below. As used in Table 3, CHI refers to one or more of the following comorbidities: acquired immune deficiency syndrome (AIDS), Cirrhosis, Leukemia, Lymphoma, and a prior tissue Transplant received by the patient. The last three rows of Table 3 assign greater weights to provide for cumulative effects on a patient's physiology associated with the patient concurrently being subject to particular combinations of comorbidities.

TABLE 3

| Comorbidity | Weight |
| --- | --- |
| Bleeding | 4.1 |
| Stroke | 3.5 |
| Heart Fail | 3.2 |
| CHIs | 2.9 |
| Neuromusc | 2.6 |
| Dementia | 2.9 |
| COPD | 2.3 |
| Stroke and Bleeding | additional 5.3 |
| Stroke and COPD | additional 2.0 |

TABLE 3-continued

| Comorbidity | Weight |
| --- | --- |
| CHIs and Heart Fail | additional 2.5 |

For example, prior to being admitted to a health care facility, a patient previously experienced a stroke. In addition, the patient is currently experiencing cirrhosis and chronic obstructive pulmonary disease (COPD). A CI score for the patient of this example may be determined as follows: 3.5 weight for the stroke+2.9 weight for CHIs (i.e. the cirrhosis)+2.3 weight for COPD. Furthermore, an additional 2.0 weight would be added to the patient's CI score for the combination of stroke and COPD, making the total points=10.7. If a multiplier of 10 is used, the CI score for this patient would be 107. In some embodiments a different multiplier may be used.

In an optional step 430, a support index (SI) score for the patient is received and/or determined. When used with a pSIS as a component of an overall SOI score for a patient, the SI score accounts for effects that certain medications and/or medical procedures administered to a patient (e.g. within the initial twenty-four hours from admission) have on the patient's physiology. In embodiments where a SI score is used, the SI score for a patient is determined by summing weights assigned to one or more support variables identified in an electronic medical record associated with the patient. Additionally, in some embodiments, a multiplier may be applied to the summation of weights assigned to the one or more identified support variables (e.g. summation of weights*10).

In another embodiment, the one or more support variables and associated weights for each that are used to determine the SI score are shown in Table 4 below. As shown by Table 4, administering some medications and/or medical procedures may result in a negative weight being assigned. This accounts for evidence that these medications and/or medical procedures correspond with a reduced mortality risk. In the embodiment of Table 4, five support variables used to determine the SI score may be based on medications and five support variables may be based on medical procedures. In other embodiments, different combinations of medication support variables and medical procedure support variables may be used.

TABLE 4

| Variable | Weight |
| --- | --- |
| Pacemaker | −3.1 |
| Intubated | 1.6 |
| Mechanical Ventilation | 7.7 |
| BiPap | 3.2 |
| Dialysis | 1.3 |
| Anti-Arrhythmic Meds | −1.2 |
| Inotrope | 2.0 |
| Vasopressor given IV | 4.0 |
| Antibiotics given IV | 1.5 |
| Insulin given IV | 1.7 |

For example, prior to being admitted to a health care facility, a patient previously had a pacemaker inserted. Also, during an initial twenty-four hour period following admission, the patient is placed on Bilevel Positive Airway Pressure (BiPap) and receives intravenous (IV) insulin. An SI score for the patient of this example may be determined as follows: −3.1 weight for the pacemaker+3.2 weight for the BiPap+1.7 weight for the insulin given IV, for a combined score of 1.8. If a multiplier of 10 is used, the SI score for this patient would be 18.0. In some embodiments a different multiplier may be used.

In step 440, an overall SOI score is determined for the patient by summing the derived pSIS and one or more of the CI score and/or the SI score. Additionally, in some embodiments, a multiplier may be applied to the summation of derived component scores (e.g. pSIS, CI score, and/or SI score) or to one or more of the derived components scores prior to summation. In these embodiments, the multiplier may serve to normalize the overall SOI score to a range of 0 to 100. Additionally or in the alternative, prior to summation, a pSIS multiplier may be applied to a derived pSIS score, a CI multiplier may be applied to a derived CI score, and/or an SI multiplier may be applied to a derived SI score. For example, a pSIS multiplier of 0.65 may be applied to a derived pSIS score, a CI multiplier of 0.20 may be applied to a derived CI score, and/or an SI multiplier of 0.25 may be applied to a derived SI score. In this example, an overall SOI score could be determined as: 0.65*determined pSIS+ 0.20*determined CI score+0.25*determined SI score.

Furthermore, if one or more derived component scores falls below (or above) an associated threshold value, a predetermined replacement score may be substituted for the derived component score. For example, a pSIS replacement score of 160 may be substituted for a derived pSIS score that is greater than 160, a CI replacement score of 180 may be substituted for a derived CI score that is greater than 180, and/or an SI replacement score of −20 may be substituted for a derived SI score that is less than −20. In an embodiment, an overall severity of illness replacement score of 100 may be substituted for an overall severity of illness derived score greater than 100.

Using the example scores for the fictional patients above with a derived pSIS of 95, a derived CI score of 107, and a derived SI score of 18, the fictional patient's overall SOI score may be 87.65 (~0.65*95+0.20*107+0.25*18).

Figure 5:
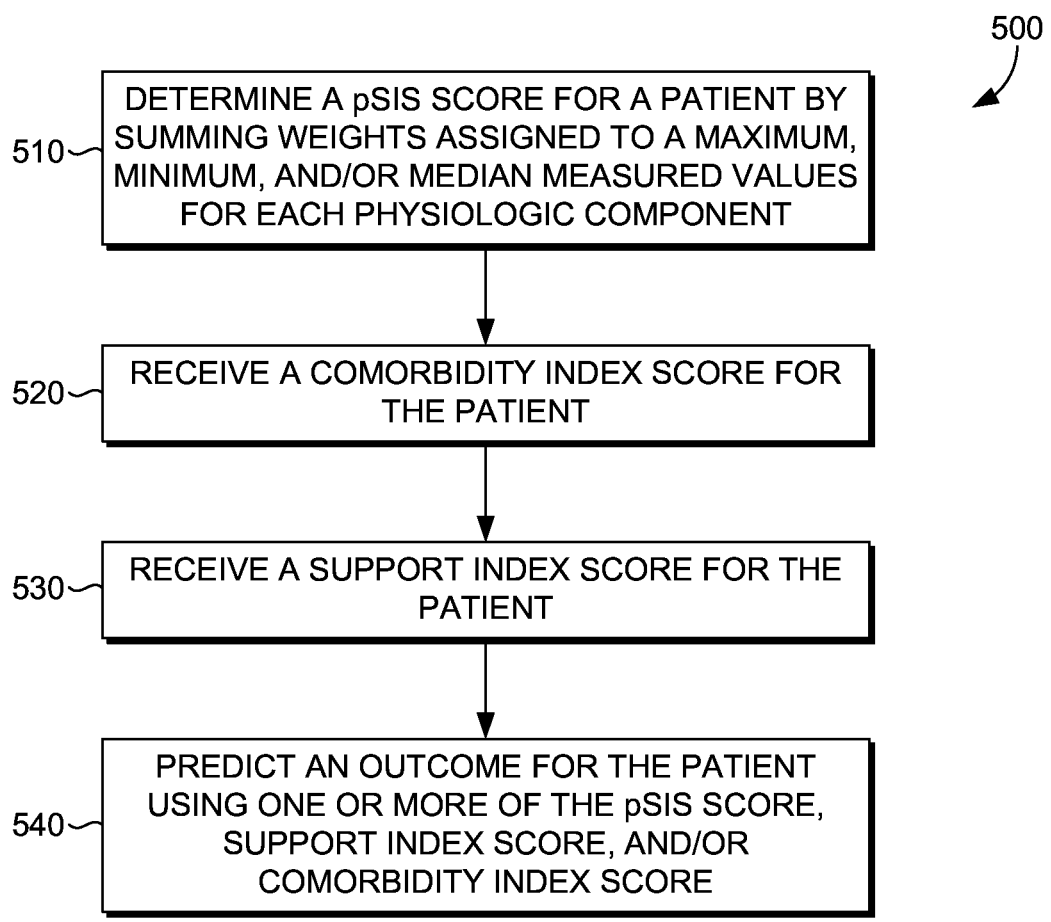
FIG. 5 is a flow diagram showing an exemplary method for predicting an outcome for a patient admitted to an acute care healthcare facility using a pSIS as a variable in predictive equations, in accordance with various embodiments of the present invention.

Turning now to FIG. 5, a flow diagram is provided illustrating a method 500 for predicting an outcome for a patient admitted to an acute care healthcare facility using a pSIS as a variable in predictive equations, in accordance with various embodiments of the present invention. As discussed above, a pSIS, may be utilized as a variable in a predictive equation to predict an outcome for the patient. Initially, in step 510, a pSIS and/or an updated pSIS is determined in accordance with method 300.

In an optional step 520, a comorbidity index (CI) score for the patient is received. When used with a pSIS as a variable in equations to predict an outcome for a patient, the CI score accounts for effects that comorbidities have on a patient's physiology. In embodiments where a CI score is used, the CI score for a patient may be determined by summing weights assigned to one or more comorbidity variables identified in an electronic medical record associated with the patient. Additionally, in some embodiments, a multiplier may be applied to the summation of weights assigned to the one or more identified comorbidity variables (e.g. summation of weights*10). An example of the one or more comorbidity variables and associated weights for each that are used to determine the CI score are shown in Table 3 above.

In an optional step 530, a support index (SI) score for the patient is received and/or determined. When used with a pSIS as a variable in equations to predict an outcome for a patient, the SI score accounts for effects that certain medications and/or medical procedures administered to a patient (e.g. within the initial twenty-four hours from admission) have on the patient's physiology. In embodiments where a SI score is used, the SI score for a patient is determined by summing weights assigned to one or more support variables identified in an electronic medical record associated with the patient. Additionally, in some embodiments, a multiplier may be applied to the summation of weights assigned to the one or more identified support variables (e.g. summation of weights*10). An example of the one or more support variables and associated weights for each that are used to determine the SI score are shown in Table 4 above.

In step 540, a predicted outcome for the patient may be determined using the derived pSIS and one or more of the CI score and/or the SI score as variables in an appropriate predictive equation. Exemplary predictive outcomes include: mortality risk, duration of mechanical ventilation, location of stay (e.g. within a health care facility or a specific level of care), readmission risk, discharge destination, and the like.

As can be understood, embodiments of the present invention provide computerized methods and systems for use in, e.g., a healthcare computing environment, for determining a pSIS for a patient admitted to an acute care facility. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

It will be understood by those of ordinary skill in the art that the order of steps shown in methods 300 of FIG. 3, 400 of FIG. 4, and 500 of FIG. 5 is not meant to limit the scope of the present invention in any way. In fact, the steps may occur in a variety of different sequences within embodiments hereof. Any and all such variations, and any combination thereof, are contemplated to be within the scope of embodiments of the present invention.

What is claimed is:

1. A computer system for determining a severity of illness score (pSIS) for a patient admitted to an acute care healthcare facility, the computer system comprising one or more processors coupled to a computer storage medium and communicating through a computer network with a plurality of remote computing devices, the computer storage medium having stored thereon a plurality of computer software components executable by the one or more processors, the computer software components comprising:

a receiving module that causes the one or more processors to receive data corresponding to physiologic components from one or more electronic medical records associated with the patient, the data corresponding to the physiologic components being related to vital sign measurements of the patient and common laboratory tests performed on blood samples taken from the patient, wherein the data is received in disparate formats;

a weight module that causes the one or more processors to convert the received data from the disparate formats to weights in a standard format by assigning weights to each physiologic component by: (1) randomly assigning cut-points that define intervals for each physiologic component, (2) randomly assigning a weight to each defined interval, and (3) evaluating the cut-points and associated weights based upon a fitness function until a predetermined condition is satisfied;

a determining module that causes the one or more processors to determine the pSIS for the patient by summing the weights assigned to each physiologic component, the weights associated with the physiologic components related to vital sign measurements of the patient being derived based on values consisting of deviations from normal of a minimum, a median, and a maximum measured value over a time period following the admission of the patient;

the one or more processors storing the weights and the pSIS in a data store and automatically generating and transmitting a first message including the pSIS in real-time through the computer network to the plurality of remote computing devices;

a prediction module that causes the one or more processors to predict based, at least in part, on the determined pSIS for the patient, at least one of a plurality of predefined outcomes for the patient;

the one or more processors automatically generating a second message including the plurality of predefined outcomes for the patient and transmitting the message in real-time through the computer network to the plurality of remote computer devices;

an additional data module that causes the one or more processors to receive additional data corresponding to the physiologic components from the electronic medical record;

an update module that causes the one or more processors to update the weights by converting the received additional data from the disparate formats to updated weights in the standard format and determine an updated pSIS for the patient;

the one or more processors storing the updated weights and the updated pSIS in a data store; and the one or more processors automatically generating and transmitting a third message including the updated pSIS in real-time through the computer network to the plurality of remote computing devices.

2. The computer system of claim 1, wherein the weights associated with the physiologic components related to common laboratory tests consist of values derived based on a minimum and a maximum measured value over the time period.

3. The computer system of claim 1, further comprising a comorbidity module that assigns weights for one or more comorbidities associated with the patient, wherein the receiving module further receives data corresponding to comorbidities from the electronic medical record.

4. The computer system of claim 1, wherein the one or more electronic medical records are collectively associated with all admissions of the patient to acute care healthcare facilities.

5. One or more computer hardware storage media having computer-executable instructions embodied thereon that, when executed by a computing device, cause the computing device communicating through a computer network with one or more remote computing devices to perform a method for determining a severity of illness score (pSIS) for a patient admitted to an acute care healthcare facility, the method comprising:

receiving, by the computing device, data corresponding to physiologic components from one or more electronic medical records associated with the patient, the data corresponding to the physiologic components being related to vital sign measurements of the patient, wherein the data is received in disparate formats;

converting, by the computing device, the received data from the disparate formats to weights in a standard format by assigning weights to each physiologic component by: (1) randomly assigning cut-points that define intervals for each physiologic component, (2) randomly assigning a weight to each defined interval, and (3) evaluating the cut-points and associated weights based upon a fitness function until a predetermined condition is satisfied;

determining, by the computing device, the pSIS for the patient by summing the weights assigned to each physiologic component, the weights associated with the physiologic components related to vital sign measurements being derived based on values consisting of deviations from normal for a minimum, a median, and a maximum measured value over a time period following an admission of the patient to the acute care healthcare facility;

storing, by the computing device, the weights and the pSIS in a data store;

automatically generating and transmitting, by the computing device, a first message including the pSIS in real-time through the computer network to the plurality of remote computing devices;

predicting, by the computing device, based, at least in part on the determined pSIS, at least one of a plurality of predefined outcomes for the patient; and automatically generating, by the computing device, a second message including the at least one of a plurality of predefined outcomes for the patient and transmitting the message in real-time through the computer network to the plurality of remote computer devices;

receiving, by the computing device, additional data corresponding to the physiologic components from the electronic medical record; and utilizing, by the computing device, the additional data to update the weights by converting the received additional data from the disparate formats to updated weights in the standard format and determine an updated pSIS for the patient;

storing, by the computing device, the updated weights and the updated pSIS in a data store; and automatically generating and transmitting, by the computing device, a third message including the updated pSIS in real-time through the computer network to the plurality of remote computing devices.

6. The one or more computer hardware storage media of claim 5, wherein the data is further associated with physiologic components related to common laboratory tests on a blood sample taken from the patient, and wherein the weights associated with each common laboratory test consist of values that are derived based on a minimum and a maximum measured value over the time period.

7. The one or more computer hardware storage media of claim 6, wherein the data associated with the common laboratory tests consists of a sodium level, a platelet count, and a hematocrit measurement.

8. The media of claim 5, wherein the method further comprises using the pSIS to trigger at least one alert for at least one clinician associated with the patient's physiology.

9. The one or more computer hardware storage media of claim 5, wherein the data associated with the vital sign measurements of the patient consist of a respiratory rate measurement, a heart rate measurement, a mean arterial pressure measurement, and a body temperature measurement.

10. The one or more computer hardware storage media of claim 5, wherein the method further comprises receiving weights assigned to one or more comorbidities associated with the patient, and wherein the data is further associated with comorbidities from the electronic medical record.

11. The one or more computer hardware media of claim 5, wherein the at least one of the plurality of predefined outcomes for the patient comprises at least one of a length of stay for the patient or hospital mortality when the time period is twenty-four hours.

12. A method performed by a server having at least one processor and communicating through a computer network with one or more remote computing devices for determining a severity of illness score (pSIS) for a patient admitted to an acute care healthcare facility, the method comprising:
receiving, by the processor, data corresponding to physiologic components from one or more electronic medical records associated with the patient, the data corresponding to the physiologic components being related to vital sign measurements of the patient and common laboratory tests performed on blood samples taken from the patient, wherein the data is received in disparate formats;
converting, by the processor, the received data from the disparate formats to weights in a standard format by assigning weights to each physiologic component by: (1) randomly assigning cut-points that define intervals for each physiologic component, (2) randomly assigning a weight to each defined interval, and (3) evaluating the cut-points and associated weights based upon a fitness function until a predetermined condition is satisfied;
determining, by the processor, the pSIS for the patient by summing the weights associated with each physiologic component, the weights for the physiologic components related to vital sign measurements being derived based on a deviation from normal for a minimum, a median, and a maximum measured value over a time period following an admission of the patient to the acute care healthcare facility;
storing, by the processor, the weights and the pSIS in a data store;
automatically generating and transmitting, by the processor, a first message including the pSIS in real-time through the computer network to the plurality of remote computing devices;
predicting, by the processor, based, at least in part on the determined pSIS, at least one of a plurality of predefined outcomes for the patient;
automatically generating, by the processor, a second message including the at least one of the plurality of predefined outcomes for the patient and transmitting the message in real-time through the computer network to the plurality of remote computer devices;
receiving, by the processor, additional data corresponding to the physiologic components from the electronic medical record; and
utilizing, by the processor, the additional data to update the weights by converting the received additional data from the disparate formats to updated weights in the standard format and determine an updated pSIS for the patient;
storing, by the processor, the updated weights and the updated pSIS in a data store; and
automatically generating and transmitting, by the processor, a third message including the updated pSIS in real-time through the computer network to the plurality of remote computing devices.

13. The method of claim 12, wherein the weights for the physiologic components related to common laboratory tests consist of values that are derived based on minimum and maximum measured values over the time period.

14. The method of claim 12, wherein the data corresponding to vital sign measurements of the patient consists of a respiratory rate measurement, a heart rate measurement, a mean arterial pressure measurement, and a body temperature measurement.

15. The method of claim 12, wherein the data corresponding to the common laboratory tests performed on blood samples taken from the patient consists of a sodium level, a platelet count, and a hematocrit measurement.

16. The method of claim 12, wherein the at least one of the plurality of predefined outcomes for the patient comprises at least one of a length of stay for the patient or hospital mortality when the time period is twenty-four hours.

* * * * *